(12) United States Patent
Pyles et al.

(10) Patent No.: US 6,432,394 B2
(45) Date of Patent: *Aug. 13, 2002

(54) HAIR CONDITIONING COMPOSITIONS COMPRISING ONE OR MORE DIBASIC AMINO ACIDS

(75) Inventors: Daniel Raymond Pyles, Chicago; Joanne Crudele, Wauconda; Trefor Evans, Lombard, all of IL (US); Varsha Shah, Menasha, WI (US); Wolfgang Robert Bergmann, Long Grove, IL (US)

(73) Assignee: Unilever Home & Personal Care USA, division of Conopco, Inc, Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/294,040

(22) Filed: Apr. 19, 1999

(51) Int. Cl.$^7$ .............................. A61K 7/06; A61K 7/11; A61K 7/075; A61K 7/08

(52) U.S. Cl. ................ 424/70.122; 424/70.1; 424/70.12; 424/70.19

(58) Field of Search .............................. 424/70.1, 70.12, 424/70.122, 70.19

(56) References Cited

U.S. PATENT DOCUMENTS

| | | |
|---|---|---|
| 4,152,416 A | 5/1979 | Spitzer et al. |
| 4,542,014 A * | 9/1985 | Bresak et al. |
| 5,085,857 A | 2/1992 | Reid et al. |
| 5,968,286 A * | 10/1999 | Crudele et al. |

FOREIGN PATENT DOCUMENTS

| | | | |
|---|---|---|---|
| EP | 0747035 | | 12/1996 |
| GB | 1 209 560 | * | 10/1970 |
| GB | 2322550 | | 9/1998 |
| JP | 59031706 A | | 2/1984 |
| JP | 2247113 A | | 10/1990 |
| JP | 03-178921 A | * | 8/1991 |
| JP | 03-178922 A | * | 8/1991 |
| JP | 10175824 A | | 6/1998 |
| JP | 10175826 A | | 6/1998 |
| WO | 97/03122 | | 1/1997 |

OTHER PUBLICATIONS

Flick, Cosmetic and Toiletry Formulations, vol. 1, pp. 611, 887, 957, and 889 (1989).*

* cited by examiner

Primary Examiner—Thurman K. Page
Assistant Examiner—Humera N. Sheikh
(74) Attorney, Agent, or Firm—Matthew Boxer

(57) ABSTRACT

The present invention relates to hair conditioning shampoo compositions which includes:

1) from about 0.05 to about 5% of one or more dibasic amino acids;
2) from about 5 to about 50% of one or more surfactants;
3) from about 0.05 to about 10% of one or more silicone compounds; and
4) water.

The invention also relates to hair conditioning compositions. The invention also relates to a method for conditioning the hair, which comprises contacting said hair with a composition according to the invention.

11 Claims, No Drawings

HAIR CONDITIONING COMPOSITIONS COMPRISING ONE OR MORE DIBASIC AMINO ACIDS

BACKGROUND OF THE INVENTION

Most individuals buy and use a hair shampoo for its cleansing properties. In addition to having clean hair, a consumer also desires sufficiently-conditioned hair that holds a preset configuration. However, hair shampoos generally are formulated with highly effective anionic surfactants that primarily clean as opposed to conditioning in the hair. Anionic surfactants not only remove the dirt and soil from the hair, but also remove sebum naturally present on the surface of the hair fibers. Therefore, the desirable cleansing properties of anionic surfactants also leave the hair in a cosmetically-unsatisfactory condition. Shampoos also do not detangle wet hair and do not impart residual conditioning benefits to dry hair, such as manageability or styleability of hair sets.

In general, shampoo compositions containing anionic surfactants, or nonionic surfactants or amphoteric surfactants, leave hair with an undesirable harsh, dull and dry touch, or feel, usually called "creak", after the hair is shampooed and then rinsed with water. Furthermore, thoroughly cleansed hair also is extremely difficult to comb, in either the wet or the dry state, because the individual hair fibers tend to snarl, kink, and interlock with each other. In addition, incompletely dried hair, such as hair dried with a towel, has poor brushing properties, and after complete drying, the hair does not set well. The combing or brushing property of dry hair remains poor, and the hair has undesirable electrostatic properties in a low humidity atmosphere that causes the hair to "fly away", thereby further reducing the brushing properties of the hair.

The unsatisfactory combing or brushing property of hair immediately after shampooing, or during trimming treatments after shampooing, also causes hair damage, such as split ends or hair breakage. In addition, the natural luster and resiliency of the hair is reduced. The overall unsatisfactory condition of shampooed hair often necessitates a subsequent post-shampoo treatment of the hair with a conditioning composition to improve these undesirable physical characteristics. Conditioning compositions typically are applied separately from the hair shampoo, and usually are rinses, cream-like emulsions or lotions containing a cationic compound.

Therefore, consumer needs traditionally have been met by the application of a shampoo to cleanse the hair, followed by the application of a conditioner composition to improve wet combing. The commonly accepted method has been to shampoo the hair, followed by rinsing the hair, and then separately applying a conditioner composition, followed by a second rinse. The wet combing problem has been solved by treating shampooed hair with a conditioner composition that coats the hair shaft and causes the individual hair shafts in a tress to resist tangling and matting because of the conditioner residue retained on the shaft.

However, the need for improved compositions that condition the hair, i.e., render the hair more manageable, has long been recognized in the art. As previously discussed, it is well-known that anionic surfactants are suitable for hair shampooing, and that cationic compounds, like cationic surfactants and cationic polymers, are useful as hair conditioners. Therefore, cationic compounds that are substantive to hair often are used to complete the hair cleansing and hair conditioning cycle.

The ability of cationic compounds to adsorb to or interact with the keratinous material of the hair makes these compounds desirable for improving wet hair detangling and dry hair manageability. However, cationic compounds that adsorb particularly strongly to the hair also can reduce the elasticity, body and set of the dried hair. Therefore, new hair conditioning agents would be desirable.

The following is a list of patents in this field.

GB 2322550A
JP 10175826 A
JP 10175824 A
WO 9703122 A1
EP 747035
JP 2247113A and
JP 59031706 A.

The present invention is directed to new hair conditioning compositions that are esthetically acceptable to consumers, improves the wet combing and properties of hair, and also leaves the dry hair with satisfactory cosmetic and physical properties, including, in particular, feel, less hair coating, manageability, body, condition of the ends and set.

SUMMARY OF THE INVENTION

The invention relates to hair conditioning compositions (both conditioners and shampooing conditioners) that comprise a dibasic amino acid.

The present invention relates a method for conditioning hair which comprises contacting hair with compositions of the invention.

DETAILED DESCRIPTION OF THE INVENTION

Unless indicated otherwise, as used herein, % means weight %. The starting materials set forth herein are either known or can be prepared in accordance with known methods. Compositions of the invention can be prepared by methods known in the art such as those set forth in the Reid and Murray patent, U.S. Pat. No. 5,085,857, issued Feb. 4, 1992, which is hereby incorporated by reference.

The present invention relates to a hair conditioner which comprises a dibasic amino acid. Two amino acids used in compositions of the invention are arginine and lysine. Both provide significant increases in the conditioning benefits of a conditioning shampoo, that is, both of the above dibasic amino acids serve as conditioning agents. The other dibasic amino acids recited herein also serve as conditioning agents.

Lysine, which has a second amino group at the epsilon position on its aliphatic chain; and arginine which has a guanidino group are useful in compositions of the invention. Mixtures of these two amino acids or their derivatives, such as, 6-N-Methyllysine and 5-hydroxylysine, are also useful in conditioning compositions of the invention. In addition, other amino acids with a dibasic character, such as those found in plants may be used. Non-limiting examples of these are alpha, gamma diaminobutyric acid and ornithine both of which have a second amino group on their aliphatic chain.

Conditioning shampoo compositions of the invention comprise ingredients in the following ranges of weight percents:

1) from about 0.05 to about 5% of one or more dibasic amino acids;
2) from about 5 to about 50% of one or more surfactants;
3) from about 0.05 to about 10% of one or more silicone compounds; and
4) water.

More preferred ranges of ingredients for these materials are as follows:
1) from about 1.0 to about 2.0% of one or more dibasic amino acids;
2) from about 10 to about 25% of one or more surfactants;
3) from about 0.1 to about 5.0% of one or more silicone compounds; and
4) water.

Dibasic Amino Acids

The amino acids which can be used in the compositions of the invention include arginine; lysine; 6-N-Methyllysine; 5-hydroxylysine; alpha, gamma diaminobutyric acid and ornithine; and the like.

Surfactants

The compositions according to the invention comprise one or more surfactants selected from the group consisting of anionic, nonionic, zwitterionic or amphoteric surfactants or mixtures thereof.

Suitable anionic surfactants include alkyl sulphates, alkyl ether sulphates, alkaryl sulphonates, alkanoyl isethionates, alkyl succinates, alkyl sulphosuccinates, n-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and preferably contain 2 to 3 ethylene oxide units per molecule.

Non-limiting examples of suitable anionic surfactants include sodium oleyl succinate, ammonium lauryl sulphosuccinate, ammonium lauryl sulphate, sodium dodecylbenzene sulphonate, triethanolamine dodecylbenzene suphonate, sodium cocyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Non-limiting examples include coco mono- or di-ethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Non-limiting examples include lauryl amine oxides, cocodimethyl sulphopropyl betaine and preferably lauryl betaine, cocamidopropyl betaine and sodium cocamphopropionate.

One or more surfactants are present in shampoo compositions of the invention in an amount of from 0.1 to 50% by weight, preferably from 0.5 to 30% by weight. Generally, the surfactants are present in shampoo compositions of the invention in an amount of from 0.1 to 50%, preferably from 5 to 30%, more preferably from 10% to 25% by weight.

Silicone Compounds

The shampoo composition of the invention also comprises one or more insoluble, non-volatile silicones, which may be one or more polyalkyl siloxanes, one or more polyalkylaryl siloxanes, or mixtures thereof. The silicone or silicones are insoluble in the aqueous matrix of the composition and therefore are present in an emulsified form, with the silicone(s) present as dispersed particles.

Suitable polyalkyl siloxanes include polydimethyl siloxanes which have the CTFA designation dimethicone, having a viscosity of from 5 to 100,000 centistokes at 25° C. These siloxanes are available commercially from the General Electric Company as the Viscasil series and from Dow Corning as the DC 200 series. The viscosity can be measured by means of a glass capillary viscometer as set out further in Dow Corning Corporate Test Method CTM004 Jul. 20, 1970.

Also suitable is polydiethyl siloxane.

The polyalkylaryl siloxanes which may be used in the compositions of the invention include polymethylphenyl polysiloxanes having a viscosity of from 15 to 65 centistokes at 25° C. The siloxanes are available commercially from the General Electric Company as SF1075 methyl phenyl fluid or from Dow Corning as 556 Cosmetic Grade Fluid.

Also suitable are silicone gums, such as those described in U.S. Pat. No. 4,152,416 (Spitzer), and on General Electric Silicone Rubber product Data Sheet SE 30, SE 33, SE 54 and SE76. U.S. Pat. No. 4,152,416 (Spitzer), is hereby incorporated by reference. "Silicone gum" denotes polydiorganosiloxanes having a molecular weight of from 200,000 to 1,000,000 and specific non-limiting examples include polydimethyl siloxane polymers, polydimethyl siloxane/diphenyl/methylvinylsiloxane copolymers, polydimethylsiloxane/methylvinylsiloxane copolymers and mixtures thereof.

Amino functional silicones which have the CTFA designation amodimethicone, are also suitable for use in the compositions of the invention, as are polydimethyl siloxanes having hydroxyl end groups (which have the CTFA designation dimethiconol).

Optional Ingredients

Nonionic surfactants

Examples of nonionic emulsifiers or surfactants which can be included in the compositions of the invention are alkylphenol ethoxylates, e.g., nonylphenol ethoxylates nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

Quaternary Ammonium Conditioning Compounds

In addition to the dibasic amino acid(s) which are included as conditioning agents, the following quaternary ammonium compounds, which are also conditioning agents, can be included in the hair conditioning compositions of the invention: quaternary ammonium compounds of the formula:

wherein $R^1$, $R^2$, and $R^3$ are C1 to C3 alkyl groups and $R^4$ is a C16 or greater alkyl group and $X^-$ is chloride, bromide methosulfate, ethosulfate, nitrate or tosylate. Non-limiting examples of these monoalkyl quaternary ammonium compounds are:
cetyltrimethyl ammonium chloride;
stearyltrimethyl ammonium chloride;

behenetrimethyl ammonium chloride;
cetrimonium chloride;
soytrimonium chlorde;
tallowtrimonium chloride;
behentrimethylammonium methosulfate;
PEG-2 Olealmonium chloride;
palmityltrimethylammonium chloride;
hydrogenated tallowtrimethylammonium chloride;
hydrogenated tallowtrimethylammonium bromide;
hydrogenated tallowtrimethylammonium methosulfate;
cetrimonium tosylate; and
eicosyltrimethylammonium chloride.

The following quaternary ammonium compounds can also be included in the hair conditioning compositions of the invention: quaternary ammonium compounds of the formula:

wherein $R^5$, and $R^6$ are C1 to C3 alkyl groups and $R^7$ and $R^8$ are a C16 or greater alkyl groups and $X^-$ is chloride, bromide methosulfate, ethosulfate, nitrate or tosylate. Non-limiting examples of these dialkyl quaternary ammonium compounds are:

dicetyldimethylammonium chloride;
distearydimethylammonium chloride;
dipalmityldimethylammonium chloride;
dihydrogenatedtallowdimethylammonium chloride;
ditallowdimethylammonium chloride;
dihydrogenatedtallowdimethylammonium bromide; and
dihydrogenatedtallowdimethylammonium methosulfate;

Cationic Conditioning Polymers

A further component of hair treatment compositions of the invention is optionally a cationic conditioning polymer which serves as a conditioning agent, in addition to the dibasic amino acid(s) that are present.

The polymer may be a homopolymer or be formed from two or more types of monomers. The molecular weight of the polymer will generally be between 5,000 and 10,000,000, typically at least 10,000 and preferably in the range 100,000 to about 2,000,000. The polymers will have cationic nitrogen containing groups such as quaternary ammonium or protonated amino groups, or a mixture thereof.

The cationic nitrogen-containing group will generally be present as a substituent on a fraction of the total monomer units of the cationic conditioning polymer. Thus when the polymer is not a homopolymer it can contain spacer non-cationic monomer units. Such polymers are described in the CTFA Cosmetic Ingredient Directory, 3rd Edition.

Suitable cationic conditioning polymers include, for example, copolymers of vinyl monomers having cationic amine or quaternary ammonium functionalities with water soluble spacer monomers such as (meth) acrylamide, alkyl and dialkyl (meth) acrylamides, alkyl (meth) acrylate, vinyl caprolactone and vinyl pyrrolidine. The alkyl and dialkyl substituted monomers preferably have C1–C7 alkyl groups, more preferably C1–C3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general, secondary and tertiary amines, especially tertiary, are preferred.

Amine substituted vinyl monomers and amines can be polymerized in the amine form and then converted to ammonium by quaternization.

Non-limiting cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxy-alkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyl such as the C1–C3 alkyls, more preferably C1 and C2 alkyls. Also included is guar hydroxypropyltrimonium chloride.

Non-limiting amine-substituted vinyl monomers include dialkylaminoalkyl acrylamide, and dialkylaminoalkyl methacrylamide, dialkylaminoalkyl acrylamide, and dialkylaminoalkyl methacrylamide, wherein the alkyl groups are preferably C1–C7 hyrocarbyls, more preferably C1–C3, alkyls.

The cationic conditioning polymers can comprise mixtures of monomer units derived from amine- and/or quaternary ammonium-substituted monomer and/or compatible spacer monomers.

Non-limiting cationic conditioning polymers include, for example: copolymers of 1-vinyl-2 pyrrolidine and 1-vinyl-3-methyl-imidazolium salt (e.g., Chloride salt) (referred to in the industry by the Cosmetic, Toiletry, and Fragrance Association, "CTFA" as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2-pyrrolidine and dimethylaminoethyl methacrylate (referred to in the industry by CTFA as Polyquaternium-11). The long chain acyl derivative is desirably selected from ethylene glycol stearate, alkanolamides of fatty acids having from 16 to 22 carbon atoms and mixtures thereof. Ethylene glycol distearate and Polyethylene glycol 3 distearate are preferred long chain acyl derivatives.

Depending on the type of composition employed, one or more additional ingredients conventionally incorporated into hair treatment compositions may be included in compositions of the invention. Such additional ingredients include styling agents, such as resins and hair-setting polymers, perfumes, dyes, buffering or pH adjusting agents, viscosity modifiers, opacifiers, pearlescers, preservatives, antibacterial agents, antidandruff agents, foam boosters, proteins, moisturizing agents, herb or other plant extracts and other natural ingredients.

To demonstrate the new and unexpected results achieved by the present invention, the compositions described below were prepared.

Compositions of the present invention have significantly more conditioning versus formulations used as comparisons. The following chart illustrates the conditioning properties of compositions of the invention. These compositions shown in the following chart are similar to the compositions set forth in the Reid and Murray patent, U.S. Pat. No. 5,085,857, and were made in a similar manner. The Reid and Murray patent, U.S. Pat. No. 5,085,857 is hereby incorporated by reference. The levels of Arginine Base and Lysine HCl present in these compositions is set forth in the following chart. The Instron wet combing test which is mentioned below is a test that is known in the art.

Instron Wet Combing

| Formula No. | Arginine Base wt % | Lysine HCl wt % | Instron WC Force gm force |
|---|---|---|---|
| A(Control) | 0.01 | 0 | 25.3 |
| B(Control) | 0 | 0.01 | 25.3 |
| G | 0 | 0.25 | 24.2 |
| F | 0 | 0.5 | 23.9 |
| E | 0 | 1 | 23.9 |
| D | 0 | 2 | 21.5 |
| C | 2 | 0 | 21.4 |

As evidenced by the above table, increasing levels of Lysine or Arginine decrease the wet combing force as shown by the Instron method, indicating enhanced conditioning.

In the following chart, The Instron Wet Combing data is correlated with Sensory Descriptive Testing. These compositions shown in the following chart are similar to the compositions set forth in the Reid and Murray patent, U.S. Pat. No. 5,085,857, and were made in a similar manner.

Instron Wet Combing & Sensory Descriptive Test

| Ingredient | Formula H (Control) | Formula I |
|---|---|---|
| Water | qs | qs |
| Sodium Laureth Sulfate (2 Moles), 25% | 56 | 56 |
| Cocamidopropyl Betaine, 30% | 6.7 | 6.7 |
| Carbomer | .4 | .4 |
| Dimethiconol, 50%, & TEA-Dodecylbenzylsulfonate, 1% | 4 | 4 |
| Propylene Glycol | .5 | .5 |
| Guar Hydroxypropyltrimonium Chloride | .1 | .1 |
| L-Arginine Base | .01 | — |
| L-Lysine HCl | — | 2 |
| Sodium Glutamate | 2 | — |
| Other[1] | qs | qs |
| Wet Combing Force (gm force) | 19.2 | 15.3 |
| Sensory Descriptive Test | | |
| Wet Detangling | 67.2 | 71.7 |
| Wet Combing | 64.4 | 68.1 |

[1]Preservatives, chelating agents, pH adjusters, viscosity modifiers and other minor ingredients.

Formula I with 2% L-Lysine HCL, a dibasic amino acid, shows better Wet Combing (lower force) versus formula H with 2% Sodium Glutamate. Also formula I performed better (higher score) in a Sensory Descriptive Test (tresses) versus formula H in Wet Detangling and Wet Combing. Sensory descriptive ratings which are higher indicate easier/better performance on the cited attributes of wet detangling and wet combing. The Sensory Descriptive Tests were run by methods known in the art.

Several amino acids were further investigated for their ability to enhance wet combing. The following charts summarize.

| Ingredient | Formulation J |
|---|---|
| Water | Qs |
| Sodium Laureth Sulfate (2 Moles), 25% | 56 |
| Cocamidopropyl Betaine, 30% | 6.7 |
| DC 2-1391 Emulsion, 25% | 3.2 |
| Other[1] | Qs |

Other[1] = Preservatives, Chelating Agents, pH adjusters, viscosity modifiers and other minor ingredients.

Various different amino acids were introduced into Formulation J. The outcome of the Instron wet combing study is given in the chart below.

Instron Wet Combing Study

| Formula | Amino acid | gram force |
|---|---|---|
| J | | 25.7 |
| L | 2% L-Arginine | 23.2 |
| M | 2% L-Lysine HCl | 23.7 |
| N | 2% L-Alanine | 26.0 |
| O | 2% L-Histidine | 25.2 |
| P | 2% L-Phenylalanine | 25.5 |
| Q | 2% L-Proline | 25.6 |
| R | 2% L-Glycine | 25.4 |
| S | 2% Sodium Glutamate | 25.4 |

This chart clearly shows that only dibasic amino acids, Arginine and Lysine, formulas L and M lower the wet combing force relative to the control (which is Formula J).

What is claimed is:

1. A hair shampoo conditioning composition which comprises:
   a) from about 0.5 to about 5% of one or more dibasic amino acids;
   b) from about 5 to about 50% of one or more surfactants;
   c) from about 0.05 to about 10% of one or more silicone compounds; and
   d) water.

2. A composition according to claim 1, which comprises:
   a) from about 0.5 to about 2.0% of one or more dibasic amino acids;
   b) from about 10 to about 25% of one or more surfactants;
   c) from about 0.1 to about 5% of one or more silicone compounds; and
   d) water.

3. A composition according to claim 1 wherein said one or more dibasic amino acids is lysine.

4. A composition according to claim 1 wherein said one or more dibasic amino acids is arginine.

5. A composition according to claim 1 wherein the dibasic amino acid agent is selected from the group consisting of arginine; lysine; 6-N-Methyllysine; 5-hydroxylysine; alpha, gamma diaminobutyric acid; ornithine; and mixtures thereof.

6. A hair conditioning composition which comprises:
   a) from about 0.05 to about 2% of one or more dibasic amino acids;
   b) from about 0.1 to about 10% of one or more surfactants;
   c) from about 0.05 to about 10% of one or more silicone compounds; and
   d) water.

7. A composition according to claim 6 wherein said dibasic amino acid is lysine.

8. A method for conditioning hair which comprises contacting said hair with a composition according to claim 1.

9. A method for conditioning hair which comprises contacting said hair with a composition according to claim 6.

10. A hair shampoo conditioning composition which comprises:
   (a) from about 0.05 to about 5% of one or more dibasic amino acids;
   (b) from about 5 to about 50% of one or more surfactants;
   (c) from about 0.05 to about 10% of one or more silicone compounds; and
   (d) water, wherein said composition is free of a cationic conditioning polymer.

11. A hair shampoo conditioning composition according to claim 10, wherein said dibasic amino acid is lysine; and said silicone compound is dimethicone, 50% and TEA-dodecylbenzylsulfonate, 1%.

* * * * *